(12) United States Patent
Feldman et al.

(10) Patent No.: US 12,171,408 B2
(45) Date of Patent: Dec. 24, 2024

(54) SYSTEMS AND METHODS FOR CORONARY OCCLUSION TREATMENT

(71) Applicant: Research Development Foundation, Carson City, NV (US)

(72) Inventors: Marc D. Feldman, San Antonio, TX (US); Thomas E. Milner, Elgin, TX (US); Nitesh Katta, Austin, TX (US); Arnold Estrada, Austin, TX (US); Meagan Oglesby, San Antonio, TX (US); Andrew Giles Cabe, San Antonio, TX (US); Mehmet Cilingiroglu, Little Rock, AR (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 18/058,987

(22) Filed: Nov. 28, 2022

(65) Prior Publication Data

US 2023/0320576 A1    Oct. 12, 2023

Related U.S. Application Data

(62) Division of application No. 16/150,554, filed on Oct. 3, 2018, now Pat. No. 11,517,374.

(Continued)

(51) Int. Cl.
*A61B 1/04* (2006.01)
*A61B 1/00* (2006.01)
(Continued)

(52) U.S. Cl.
CPC ............... *A61B 1/04* (2013.01); *A61B 1/00* (2013.01); *A61B 5/0066* (2013.01);
(Continued)

(58) Field of Classification Search
CPC .......... A61B 1/04; A61B 1/00; A61B 5/0066; A61B 5/0084; A61B 5/0261; A61B 18/245; A61B 2090/3614; A61B 2018/00702; A61B 2018/00761; A61B 2018/00904; A61B 2018/00982; A61B 2218/005;
(Continued)

(56) References Cited

U.S. PATENT DOCUMENTS

| 4,747,405 A | 5/1988 | Leckrone |
| 4,765,330 A | 8/1988 | Bach |

(Continued)

FOREIGN PATENT DOCUMENTS

| CA | 2575812 A1 * | 2/2006 | |
| CA | 2728845 A1 * | 1/2010 | ....... A61B 17/22032 |

(Continued)

OTHER PUBLICATIONS

"Spectranetics Initiates Research Collaboration to Combine Imaging Technology With Its Laser Devices", PR Newswire, published May 18, 2006.

(Continued)

*Primary Examiner* — Michael J Lau
(74) *Attorney, Agent, or Firm* — Parker Highlander PLLC (57) ABSTRACT

Exemplary embodiments of the present disclosure include systems and methods for treatment of occlusions, including coronary artery chronic total occlusions.

23 Claims, 6 Drawing Sheets

Related U.S. Application Data (60) Provisional application No. 62/567,491, filed on Oct. 3, 2017.

(51) Int. Cl.

| | | |
|---|---|---|
| *A61B 5/00* | (2006.01) | |
| *A61B 5/026* | (2006.01) | |
| *A61B 18/24* | (2006.01) | |
| A61B 17/00 | (2006.01) | |
| A61B 18/00 | (2006.01) | |
| A61B 90/00 | (2016.01) | |
| A61M 25/00 | (2006.01) | |
| A61M 25/09 | (2006.01) | |

(52) U.S. Cl.
CPC .......... *A61B 5/0084* (2013.01); *A61B 5/0261* (2013.01); *A61B 18/245* (2013.01); *A61B 2017/00057* (2013.01); *A61B 2017/00194* (2013.01); *A61B 2018/00702* (2013.01); *A61B 2018/00761* (2013.01); *A61B 2018/00904* (2013.01); *A61B 2018/00982* (2013.01); *A61B 2090/3614* (2016.02); *A61B 2218/005* (2013.01); *A61B 2218/007* (2013.01); *A61M 25/0026* (2013.01); *A61M 25/09* (2013.01)

(58) Field of Classification Search
CPC .... A61B 2218/007; A61B 2017/00057; A61B 2017/00194; A61M 25/0026; A61M 25/09
USPC ........................................................ 600/108
See application file for complete search history.

(56) References Cited

U.S. PATENT DOCUMENTS

| | | | | |
|---|---|---|---|---|
| 4,869,246 | A * | 9/1989 | Adair .................... | A61M 25/10 |
| | | | | 606/7 |
| 5,071,422 | A | 12/1991 | Watson | |
| 5,634,897 | A * | 6/1997 | Dance .................... | A61B 17/22 |
| | | | | 604/35 |
| 5,954,713 | A * | 9/1999 | Newman ............ | A61B 17/3207 |
| | | | | 606/15 |
| 6,595,987 | B1 | 7/2003 | Negus | |
| 6,712,798 | B2 | 3/2004 | Constantz | |
| 7,004,173 | B2 | 2/2006 | Sparks et al. | |
| 7,734,332 | B2 | 6/2010 | Sher | |
| 8,147,414 | B2 | 4/2012 | Abraham | |
| 8,241,273 | B2 | 8/2012 | Whayne et al. | |
| 9,125,562 | B2 | 9/2015 | Spencer et al. | |
| 9,283,034 | B2 | 3/2016 | Katoh et al. | |
| 9,486,143 | B2 | 11/2016 | Hoseit et al. | |
| 9,557,156 | B2 | 1/2017 | Kankaria | |
| 9,572,492 | B2 | 2/2017 | Simpson et al. | |
| 2001/0025190 | A1 | 9/2001 | Weber et al. | |
| 2002/0161427 | A1* | 10/2002 | Rabkin .................... | A61F 2/95 |
| | | | | 623/1.11 |
| 2004/0097804 | A1* | 5/2004 | Sobe .................. | A61B 17/3207 |
| | | | | 600/424 |
| 2004/0102766 | A1 | 5/2004 | Poleo | |
| 2004/0143286 | A1* | 7/2004 | Johnson .................. | A61F 2/954 |
| | | | | 623/1.11 |
| 2005/0251116 | A1* | 11/2005 | Steinke ................ | A61B 5/0066 |
| | | | | 606/14 |
| 2005/0283143 | A1* | 12/2005 | Rizoiu .................... | A61B 18/20 |
| | | | | 604/35 |
| 2006/0052661 | A1 | 3/2006 | Gannot et al. | |
| 2006/0241503 | A1* | 10/2006 | Schmitt ................ | G01B 9/0205 |
| | | | | 600/478 |
| 2006/0271154 | A1* | 11/2006 | Woodall .................. | A61F 2/958 |
| | | | | 623/1.11 |
| 2008/0154172 | A1* | 6/2008 | Mauch .............. | A61M 25/0068 |
| | | | | 604/164.13 |
| 2009/0240277 | A1 | 9/2009 | Connors et al. | |
| 2010/0010355 | A1 | 1/2010 | Kassab | |
| 2010/0063534 | A1 | 3/2010 | Kugler et al. | |
| 2010/0179522 | A1 | 7/2010 | Companion et al. | |
| 2010/0305452 | A1* | 12/2010 | Black .................... | A61B 5/6852 |
| | | | | 600/476 |
| 2011/0218528 | A1 | 9/2011 | Ogata et al. | |
| 2012/0035442 | A1 | 2/2012 | Barman et al. | |
| 2014/0200438 | A1 | 7/2014 | Millett et al. | |
| 2014/0276683 | A1 | 9/2014 | Hendrick | |
| 2014/0308210 | A1 | 10/2014 | Mangat et al. | |
| 2014/0350523 | A1 | 11/2014 | Dehdashtian et al. | |
| 2015/0099984 | A1* | 4/2015 | Kankaria ............. | A61B 5/0066 |
| | | | | 600/478 |
| 2015/0342681 | A1 | 12/2015 | Lee | |
| 2016/0120558 | A1* | 5/2016 | Brady ..................... | A61F 2/013 |
| | | | | 606/159 |
| 2016/0206373 | A1 | 7/2016 | Chen et al. | |
| 2016/0262777 | A1* | 9/2016 | Stigall ...................... | A61N 7/00 |
| 2016/0317174 | A1 | 11/2016 | Dake | |
| 2017/0007162 | A1 | 1/2017 | Choi et al. | |
| 2017/0071625 | A1 | 3/2017 | Chang et al. | |
| 2017/0086860 | A1* | 3/2017 | Lee .................... | A61B 17/3207 |

FOREIGN PATENT DOCUMENTS

| | | |
|---|---|---|
| CN | 102631245 | 3/2014 |
| WO | WO 1997/009924 | 3/1997 |
| WO | WO 2001/054761 | 8/2001 |
| WO | WO 2016/180289 | 11/2016 |
| WO | WO 2017/074920 | 5/2017 |

OTHER PUBLICATIONS

Extended European Search Report issued in European Application No. 18863945.4, mailed May 31, 2021.

International Search Report and Written Opinion issued in corresponding PCT Application No. PCT/US2018/054063, mailed on Jan. 23, 2019.

Hafner et al., "What you should know about emerging techniques in revascularization", *Podiatry Today*, 22(3), <URL: https://www.podiatrytoday.com/what-you-should-know-about-emerging-techniques-in-revascularization>, Feb. 26, 2009.

Munce, "The Potential of Optical Coherence Tomography for Intravascular Imaging of Chronic Total Occlusions", Doctoral Thesis, University of Toronto, 2009.

\* cited by examiner

SYSTEMS AND METHODS FOR CORONARY OCCLUSION TREATMENT

CROSS-REFERENCE TO RELATED APPLICATION

This application is a divisional of U.S. application Ser. No. 16/150,554, filed Oct. 3, 2018, which claims priority to U.S. Provisional Application No. 62/567,491 filed Oct. 3, 2017, the entire contents of each of which are incorporated herein by reference.

BACKGROUND INFORMATION

A vascular occlusion is a blockage of a blood vessel that restricts or prevents the flow of blood through the vessel. Reduced or lack of blood flow through an occluded vessel can lead to serious health complications for the patient. Treatment of vascular occlusions includes various techniques to clear the occlusion and prevent reformation of the occlusion within the vessel. Typical treatment techniques for vascular occlusions include directing a guide wire or other component through the occluded portion, often the wall of the blood vessel to assist in the placement of a stent. In certain techniques, the stent can be expanded to create and maintain an open passage through the previously occluded region, or outside the wall of the occlusion.

While techniques have been developed to treat vascular occlusions, certain types of occlusions can present difficulties in selecting treatment options. In particular, severely occluded vessels can prevent challenges in treatment.

A particular type of vascular occlusion that presents challenges in treatment is a chronic total occlusion (CTO), which is a complete, or substantially complete, obstruction of a coronary artery. Approximately twenty-five percent of patients undergoing an angiography are found to have a CTO. With roughly two million patients undergoing a diagnostic angiography annually in the United States, CTOs present health risks for a significant number of patients.

While pharmacologic applications can be used to treat angina that patients with CTOs suffer from, these are not always successful in the elimination of angina symptoms. Medical interventional procedures are used to provide CTO treatment in cases where medication is not successful. The two primary existing procedures for addressing CTOs include coronary artery bypass grafting (CABG) and percutaneous coronary intervention (PCI). CABG is an invasive surgical procedure in which a healthy artery or vein is grafted, past the occluded coronary artery. The grafted vessel bypasses the occluded region of the coronary artery and provides a path for blood to flow to the heart muscle. CABG is a relatively expensive procedure, more traumatic to the patient with longer patient recovery times as compared to PCI.

PCI procedures typically include advancing a collapsed stent into the occluded region and expanding the stent to provide a passageway through the previously-blocked vessel. Such procedures generally involve directing a guide wire through the occluded region to allow for placement of a stent. However, in the case of CTOs, it is often not possible to direct the guide wire through the occluded region which is completely blocked. In such cases, treatment options include directing a guide wire or other components through or around the occlusion, including through the vessel wall. Specifically, many typical treatment options require directing components through the subintimal space in the vessel.

Such treatment options present significant challenges to the physician, due in part to the limited space available and associated risks presented. One of the primary challenges is directing a mechanical component past the occlusion without inadvertently perforating the vessel wall. Such a perforating of the vessel wall can lead to severe complications, such as cardiac tamponade, and it is therefore highly desirable to avoid such risks when treating patients with vascular occlusions.

In addition, such treatment options can require significant amounts of time to perform—typically up to three hours. Completing a procedure requires extreme concentration by the physician over prolonged time periods while performing extremely precise maneuvers. This can lead to physician fatigue and increase the risks of inadvertently perforating the vessel wall. Accordingly, few cardiologists are capable of, or willing to, perform PCI procedures of CTOs. The extended time periods for such procedures also result in redirection of resources (both equipment and human) normally available for other procedures.

Accordingly, systems and methods are desired that overcome these and other limitations associated with existing systems and methods.

SUMMARY

Exemplary embodiments of the present disclosure include systems and methods capable of treating vascular occlusions (e.g. restoring blood flow through the occluded region of the vessel) that address shortcomings of existing treatment options. Particular embodiments include systems and methods for treating chronic total occlusions (CTOs).

As explained in further detail below, particular embodiments allow a physician to create a pathway through a CTO without entering the subintimal space of the vessel. By avoiding the subintimal space of the vessel, the risk of perforating the vessel outer wall is greatly reduced. Exemplary embodiments can further address shortcomings of existing treatment options by reducing the time required to perform the procedure. Reduced procedure time can allow resources to be used for other procedures. By reducing risks associated with CTO treatment, embodiments of the present disclosure can potentially increase the number of physicians who can perform these procedures.

Exemplary embodiments include a device for treating a patient with a coronary artery chronic total occlusion (CTO) which includes a combination of imaging, tissue ablation, and tissue removal capabilities. In one embodiment, the device includes four lumens or apertures dedicated to different aspects of treatment: (1) imaging; (2) ablation; (3) inert gas delivery; and (4) vacuum.

For example, the device can have one lumen for a fiber utilizing imaging capability to provide visual confirmation to the user of the orientation of the probe with respect to the occlusion, to avoid the subintimal space. In a particular embodiment, the device may utilize optical coherence tomography (OCT) technology to provide imaging capabilities.

The device may have a second lumen dedicated to a tissue ablation device. In one embodiment, the tissue ablation device may be a laser (e.g. an erbium or thulium laser) configured for ablation of tissue from the occlusion.

The device may have a third lumen configured to allow inert gas delivery (e.g. $CO_2$) and a fourth lumen coupled to a low pressure source to remove debris resulting from laser tissue interaction. The removal of the ablated tissue debris from the region near the occlusion can assist in reducing heat transfer into regions near the occlusion site and maintaining effective tissue removal with the laser. The combination of visualization, ablation, and tissue removal capabilities can allow a user to open safely and effectively a pathway through the central portion of the occlusion.

This is considered a safer alternative to the existing treatment options (e.g. percutaneous coronary intervention [PCI] that attempt to create a pathway around the perimeter of the occlusion, often into the wall of the artery, which risks perforating the vessel wall.

Certain embodiments include a system comprising a catheter control system and a catheter coupled to the catheter control system, where the catheter control system comprises an imaging system, a laser, a vacuum source, and an inert gas source, and where the catheter comprises an imaging fiber coupled to the imaging system, a laser fiber coupled to the laser, a vacuum lumen coupled to the vacuum source and an inert gas lumen coupled to the inert gas source.

In particular embodiments, the laser is an Erbium-doped yttrium aluminum garnet laser (Er:YAG) laser. In some embodiments, the imaging system is an optical coherence tomography imaging (OCT) system. In specific embodiments, the catheter has an outer diameter of 1.0 mm or less. In specific embodiments, the catheter control system is configured to cycle the laser on and off, and cycle an application of inert gas from the inert gas source through the inert gas lumen. In certain embodiments, the catheter control system is configured to synchronize cycling the laser on and off with cycling inert gas from the inert gas source through the inert gas lumen, such that electromagnetic energy from the laser is applied at the same time as the application of inert gas. In particular embodiments, the catheter control system is configured to provide vacuum suction. In some embodiments, the laser has a pulse repetition rate of 0.1-1.0 kHz. In certain embodiments, the laser has a pulse repetition rate of 25 Hz-1 kHz. In specific embodiments, the laser has a pulse duration of 1-30 nanoseconds, or more specifically 2-20 nanoseconds, or more specifically 5-15 nanoseconds. In particular embodiments, the laser has a pulse duration of 20 µs to 1 ms.

In certain embodiments, the laser emits energy in a range of wavelengths from 1.0-5.0 microns, or more specifically 1.5-4.0 microns, or more specifically from 2.3-3.0 microns. In particular embodiments, the laser emits energy at a wavelength of 2.94 µm. In some embodiments, the laser has a pulse energy of 1 mJ to 100 mJ. In specific embodiments, the laser has a pulse energy of approximately 5 mJ. In certain embodiments, the laser has an average power of 1-10 W.

In particular embodiments, the imaging fiber comprises a first end, a second end, and a primary axis extending from the first end to the second end, and the imaging system rotates the imaging fiber about the primary axis of the imaging fiber. In some embodiments, the inert gas source comprises pressurized $CO_2$. In specific embodiments, during use OCT light from the imaging fiber is used to perform automated plaque characterization so that laser energy from the laser can be reduced when cutting lipid and fibrous tissue, and the laser energy from the laser can be increased when cutting calcium. In certain embodiments, during use the system is configured to provide an automated reduction in laser energy from the laser while still cutting to prevent overheating of the artery.

Particular embodiments include a method of treating a chronic total occlusion in a blood vessel, where the method comprises: deploying a guide wire to a location of the chronic total occlusion; deploying a catheter over the guide wire (where the catheter comprises a proximal end, a distal end, a plurality of lumens, and a laser fiber; the catheter is deployed over the guide wire via a first lumen in the plurality of lumens; and the distal end of the catheter is positioned at the location of the chronic total occlusion); retracting the guide wire from the first lumen in the catheter; inserting an imaging fiber into an open lumen of the catheter; visually inspecting the location of the chronic total occlusion via the imaging fiber ahead of a focus of the laser fiber; cutting material from the chronic total occlusion via the laser fiber; retracting the imaging fiber from the first lumen of the catheter; inserting the guide wire into the first lumen of the catheter and through the chronic total occlusion; and retracting the catheter from the location of the chronic total occlusion while the guide wire remains in position extending through the chronic total occlusion.

In some embodiments, the guide wire does not enter the subintimal space of the blood vessel when the guide wire is inserted through the chronic total occlusion. Specific embodiments further comprise deploying an expandable stent to the location of the chronic total occlusion, and expanding the expandable stent. Certain embodiments further comprise deploying an atherectomy catheter to the location of the chronic total occlusion, and spinning the atherectomy device to further enlarge and decalcify the total occlusion. In particular embodiments, the laser fiber comprises a lens at a distal end of the laser fiber, and removing material from the chronic total occlusion via the laser fiber comprises directing electromagnetic energy through the lens and across the chronic total occlusion. Some embodiments further comprise rotating the laser fiber to direct electromagnetic energy to different regions of the chronic total occlusion. Specific embodiments further comprise imaging via OCT light focused ahead of the rotating laser fiber to safely direct electromagnetic energy from the laser fiber to different regions of the chronic total occlusion, but away from a wall of the blood vessel. Certain embodiments further comprise delivering a pressurized inert gas to the location of the chronic total occlusion. In particular embodiments, the pressurized inert gas comprises pressurized $CO_2$. In some embodiments, removing material from the chronic total occlusion via the laser fiber comprises pulsing electromagnetic energy from the laser fiber; and delivering the pressurized inert gas to the location of the chronic total occlusion comprises pulsing the pressurized inert gas, and using a vacuum to remove laser debris liberated by the pressurized inert gas. In specific embodiments, pulsing electromagnetic energy from the laser fiber is synchronized with pulsing the pressurized inert gas and a vacuum.

In certain embodiments, electromagnetic energy is pulsed from the laser fiber at a frequency of 0.1-1.0 kHz. In particular embodiments, each laser energy pulse has a duration of 1-30 nanoseconds. In some embodiments, each laser energy pulse has a duration of 2-20 nanoseconds, or more particularly 5-15 nanoseconds, or more particularly 1.0-5.0 microns. In specific embodiments, the laser emits electromagnetic energy in a range of wavelengths from 1.5-4.0 microns, or more particularly 2.3-3.0 microns.

In certain embodiments, the laser fiber emits electromagnetic energy with a pulse repetition rate of 25 Hz-1 kHz. In particular embodiments, the laser fiber emits electromagnetic energy with a pulse duration of 20 µs to 1 ms. In some embodiments, the laser fiber emits electromagnetic energy with a wavelength of 2.94 µm. In specific embodiments, the laser fiber emits electromagnetic energy with a pulse energy of 1 mJ to 100 mJ. In certain embodiments, the laser fiber emits electromagnetic energy with a pulse energy of approximately 5 mJ. In particular embodiments, the laser fiber emits electromagnetic energy with an average power of 1-10 W.

Certain embodiments include a catheter configured to penetrate a chronic total occlusion, where the catheter comprises a proximal end; a distal end; an imaging fiber configured to transmit imaging data from the distal end of the catheter to the proximal end of the catheter; a laser fiber configured to transmit laser energy from the proximal end of the catheter to the distal end of the catheter; a vacuum lumen configured to transmit a vacuum from the proximal end of the catheter to the distal end of the catheter; and an inert gas lumen configured to transmit an inert gas from the proximal end of the catheter to the distal end of the catheter.

In particular embodiments, the imaging fiber is configured to focus imaging light at a distance D1 from the distal end; the laser fiber is configured to focus the laser energy at a distance D2 from the distal end; and D1 is greater than D2. In some embodiments, the laser fiber is configured to transmit laser energy from an Erbium-doped yttrium aluminum garnet laser (Er:YAG) laser. In specific embodiments, the imaging fiber is configured to transmit optical coherence tomography imaging data. In certain embodiments, the imaging fiber is configured to transmit optical coherence tomography imaging data for the determination of plaque composition real-time to minimize heating of the artery. Particular embodiments, further comprise a sheath configured to transmit a torque from the proximal end of the catheter to the distal end of the catheter. In certain embodiments, the sheath is a multi-filar flexible sheath.

Particular embodiments further comprise a flexible housing extending from the proximal end of the catheter to the distal end of the catheter, where: the flexible housing comprises a first lumen and a second lumen; the imaging fiber extends through the first lumen; the laser fiber extends through the second lumen; and the vacuum lumen extends through the flexible housing. In some embodiments, the pressurized inert gas lumen extends through the flexible housing. In specific embodiments, the flexible housing is a polytetrafluoroethylene (PTFE) extrusion. In certain embodiments, the inert gas lumen extends through the flexible housing. Particular embodiments further comprise an outer sheath around the flexible housing, wherein the outer sheath extends between the proximal end of the catheter and the distal end of the catheter. In some embodiments, the inert gas lumen extends through the outer sheath. In specific embodiments, the catheter has an outer diameter of 1.0 mm or less.

In certain embodiments, the laser fiber emits electromagnetic energy with a pulse repetition rate of 25 Hz-1 kHz. In particular embodiments, the laser fiber emits electromagnetic energy with a pulse duration of 20 µs to 1 ms. In some embodiments, the laser fiber emits electromagnetic energy with a wavelength of 2.94 µm. In specific embodiments, the laser fiber emits electromagnetic energy with a pulse energy of 1 mJ to 100 mJ. In certain embodiments, the laser fiber emits electromagnetic energy with a pulse energy of approximately 5 mJ. In specific embodiments, the laser fiber emits electromagnetic energy with an average power of 1-10 W.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

As used herein, the term "light source" or "laser" is understood to include any source of electromagnetic radiation, including for example, an erbium or thulium laser. It is also understood that a "first light source" and a "second light source" may originate from a single laser. For example, a laser configured for operating under a first set of parameters (e.g. wavelength, amplitude, continuous wave or continuous pulse mode) may be considered a "first light source", while the same laser configured for operating under a second set of parameters may be considered a "second light source."

Also as used herein, the term "cut" (and related terms such as "cutting", etc.) is used to refer to a process of a phase change wherein the biological material is separated into at least two portions.

As used herein, the term "coagulate" (and related terms, such as "coagulating", "coagulation", etc.) is used to refer to a process of interrupting blood flow (e.g. by damaging blood vessels so that when cut, they cannot bleed) and rearranging and/or restructuring molecular bonds in tissue without completely breaking a majority of the molecular bonds.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The patent or application file may contain at least one drawing executed in color. If applicable, copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
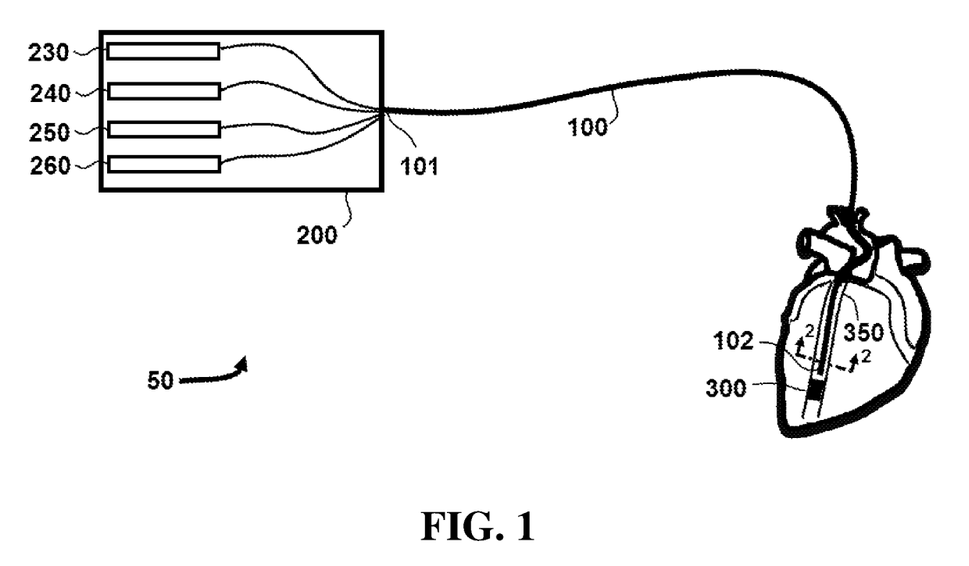
FIG. 1 shows a schematic of a system according to an exemplary embodiment during use.

Exemplary embodiments of the present disclosure include systems and methods that utilize Referring now to FIG. 1, a schematic overview of one exemplary embodiment illustrates a system 50 comprising a catheter 100 coupled to a control system 200. During operation of system 50, a proximal end 101 of catheter 100 can be coupled to control system 200, while a distal end 102 of catheter 100 can be inserted into a patient and proximal to a location within a blood vessel 350 with an occlusion 300, including for example, a coronary chronic total occlusion (CTO). As used herein, proximal end 101 and distal end 102 are not limited to each absolute end of catheter 100, but also include a portion of catheter 100 within ten percent of the length of catheter 100. Accordingly, a component or feature that is located "at" proximal end 101 or distal end 102 is understood to be located within ten percent of the length of catheter 100 of an absolute end of catheter 100.

Figure 2:
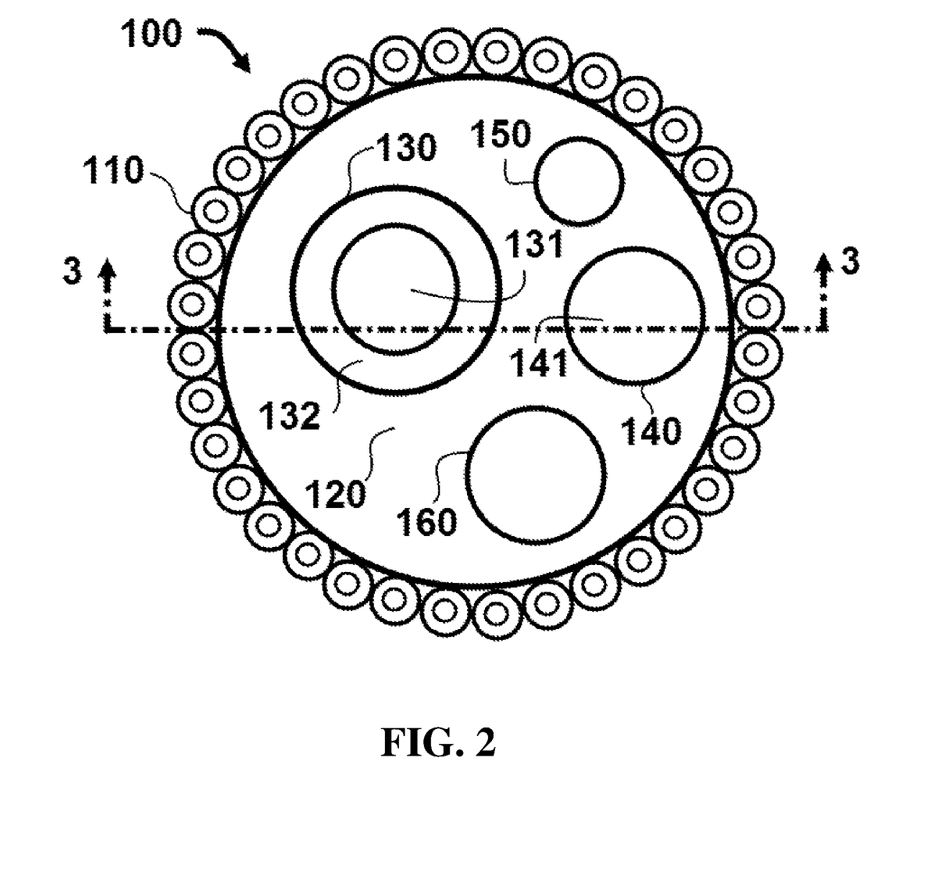
FIG. 2 shows an axial cross-section of a catheter of the embodiment of FIG. 1.
Figure 3:
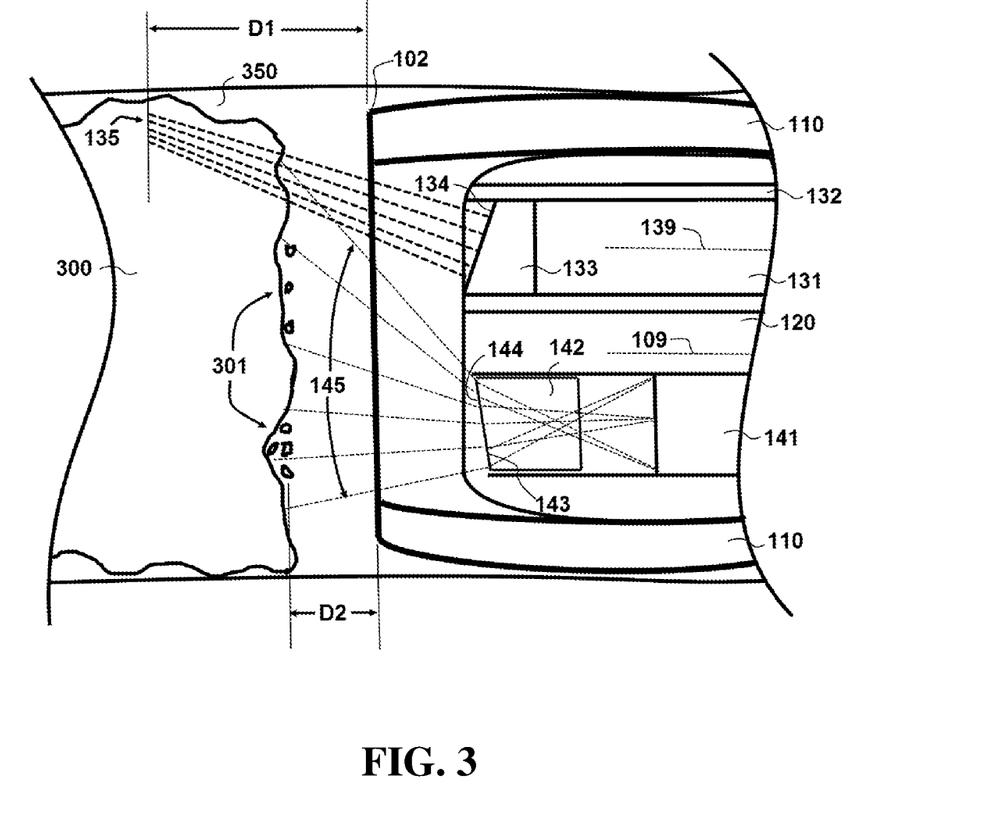
FIG. 3. shows a lateral cross-section of the component of the embodiment of FIG. 2 during use

Referring now to FIG. 2, a view of a cross-section taken along line 2-2 of FIG. 1 of one embodiment of catheter 100 is shown. FIG. 3 is a side sectional view of catheter 100 (taken along line 3-3 of FIG. 2) during use. In the embodiment shown, catheter 100 comprises a multi-filar flexible outer sheath 110 surrounding a flexible housing 120 comprising a plurality of lumens 130, 140, 150 and 160. The multi-filar flexible sheath allows advancement of the catheter inside the vessel lumen. In certain embodiments, flexible housing 120 can be configured as a polytetrafluoroethylene (PTFE) extrusion. The different lumens within flexible housing 120 can perform various functions to penetrate occlusion 300 (shown in FIG. 1).

In the embodiment shown, an imaging fiber 131 configured to allow a user to visualize surrounding tissue at distal end 102 of catheter 100 extends through lumen 130. In particular embodiments, imaging fiber 131 can be configured as an optical coherence tomography (OCT) fiber that is coupled to an OCT imaging system 230, which may be part of control system 200 or coupled to control system 200. OCT imaging systems are well known in the art, and OCT imaging system 230 is understood to include components (e.g. light sources, lenses, beam splitters, filters, cameras, processors, displays, etc.) configured to provide OCT imaging of occlusion 300 and the surrounding region via imaging fiber 131.

In addition, a torque coil 132 surrounding imaging fiber 131 also extends through lumen 130 in the illustrated embodiment. As explained in further detail below, torque coil 132 can allow a user to torque or rotate catheter 100 around its primary axis 109 (e.g. the axis extending between proximal end 101 and distal end 102). In addition, multifilar sheath 110 can allow a user to push catheter 100 along its primary axis and toward occlusion 300. The ability to rotate and push catheter 100 can allow a user to visualize the tissue surrounding distal end 102 and to penetrate occlusion 300, as explained in further detail below.

In the view shown in FIG. 2, catheter 100 comprises a laser fiber 141 extending through lumen 140. In particular embodiments, laser fiber 141 may be coupled to a laser 240, which may be a component of control system 200 or coupled to control system 200. In specific embodiments, laser 240 may be an Erbium-doped yttrium aluminum garnet laser (Er:YAG). In certain embodiments, the pulse duration of laser 240 is tunable from 20 µs to 1 ms, and the longitudinal thermal relaxation time is in the range of 10-100 µs. In particular embodiments, laser 240 is operated with a pulse duration in a range between 20 µs to several hundred µs (e.g. between 20-900 µs). In some embodiments laser 240 has a pulse energy that is tunable in a range between 1 mJ to 100 mJ. In specific embodiments, laser 240 is operated with a wavelength of 2.94 µm and a pulse energy of approximately 5 mJ. In certain embodiments, the pulse repetition rate (PRR) of laser 240 is within a range of 25 Hz to 1 kHz. During operation, the PRR value can be controlled based on the desired removal rate with feedback from the OCT imaging. In particular embodiments, laser 240 is a diode pumped Er:YAG laser with an average power that can be tuned to reach a maximum of 50 W. In specific embodiments, laser 240 may be operated in a range of 1-10 W with the preferred pulse durations and pulse energies.

In addition, catheter 100 also comprises a lumen 150 coupled to an inert gas (e.g. carbon dioxide [$CO_2$]) source 250 and a lumen 160 coupled to a vacuum source 260. In particular embodiments, inert gas source 250 and vacuum source 260 can each be components of, or coupled to, control system 200. In certain embodiments, catheter 100 may comprise a bend or curved portion near distal end 102. Such a configuration can allow a user to redirect light emitted by imaging fiber 131 or electromagnetic energy emitted by laser fiber 141 by rotating catheter 100.

Figure 4:
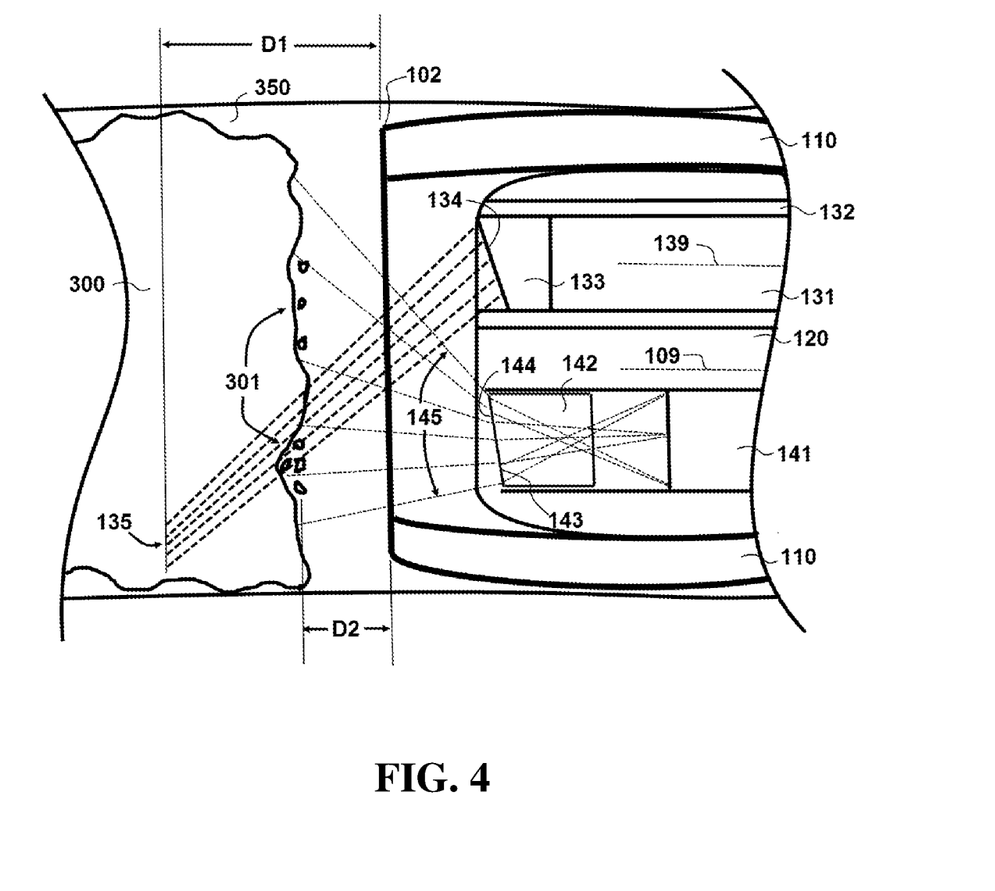
FIG. 4 shows a lateral cross-section of the component of the embodiment of FIG. 2 during use in a different position than the embodiment of FIG. 3.
Figure 5:
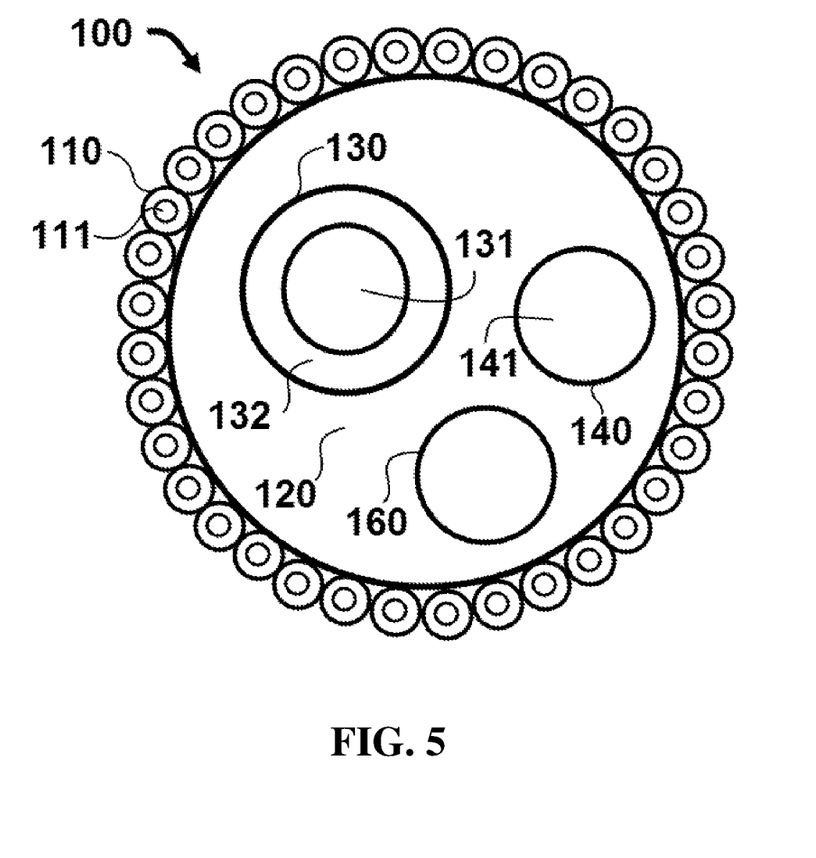
FIG. 5 shows an axial cross-section of an alternate embodiment of a catheter.

Referring now to FIG. 5, an alternate embodiment is shown that is equivalent to the embodiment of FIG. 2 in most respects. The embodiment of FIG. 5, however, does not have an internal lumen for inert gas delivery. Instead, the embodiment of FIG. 5 comprises lumens 111 within sheath 110 for delivery of the inert gas. Accordingly, the FIG. 5 embodiment does not include lumen 150, as incorporated in the embodiment of FIG. 2. The remaining components in the FIG. 4 embodiment are equivalent to those of the FIG. 2 embodiment, and are indicated with equivalent reference numbers. Accordingly, the remaining features of the embodiment shown in FIG. 5 will not be described separately and are understood to operate in a manner equivalent to that described in the discussion of the FIG. 2 embodiment. It should be noted that the embodiment described in FIG. 5 is a method to reduce the overall outer diameter of the device which can result in greater ease of use and increased safety resulting from a lower profile device.

Control system 200 and catheter 100 can be configured such that when proximal end 101 of catheter 100 is coupled to the control system 200, each of the lumens in catheter 100 are correctly aligned and coupled to the desired component within control system 200.

Figure 6:
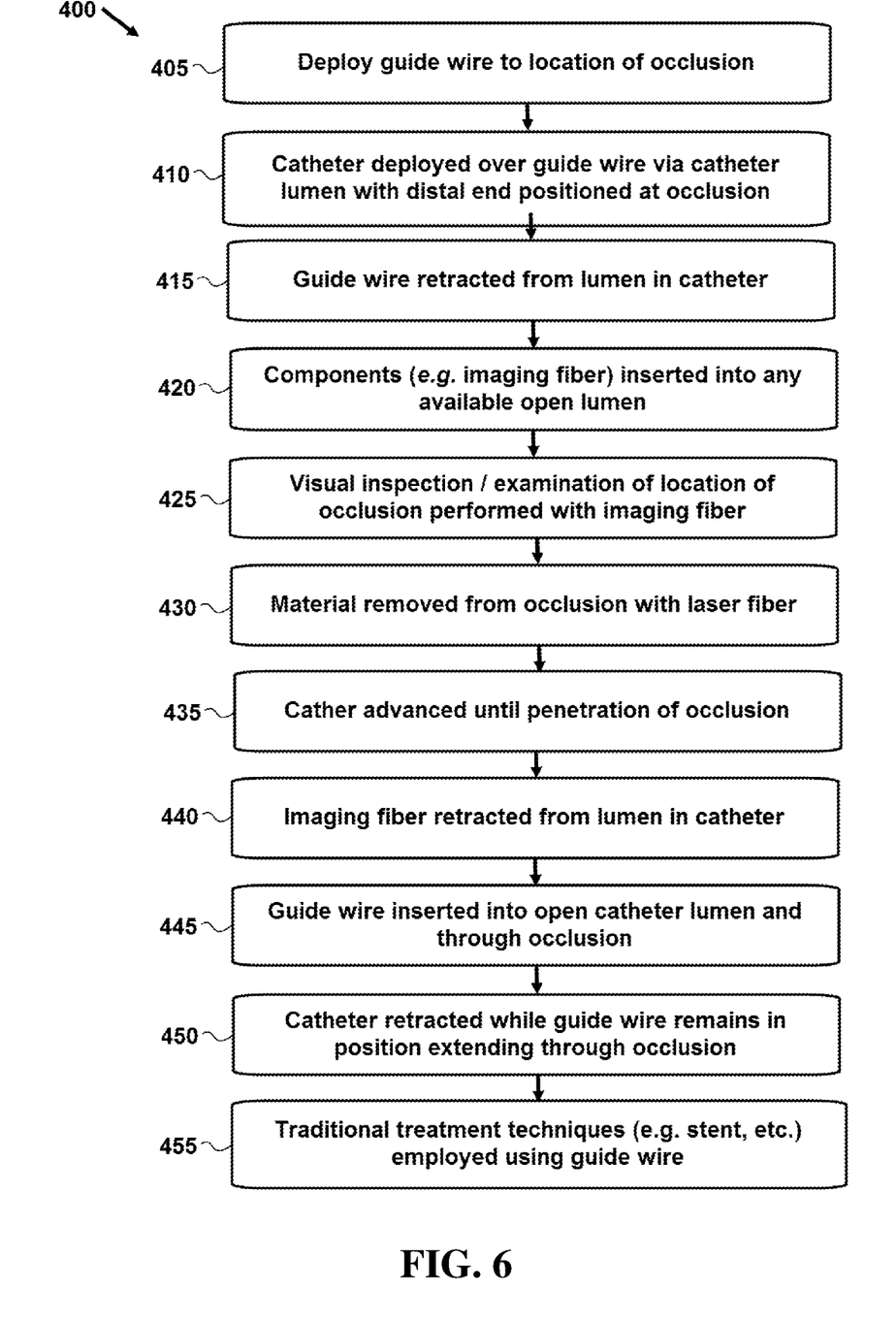
FIG. 6 shows a flowchart of one embodiment of a method of use of the embodiment of FIG. 1.

Referring now to FIG. 6, a flowchart 400 depicts an overview of one method of operation of system 50. In this embodiment, in step 405 a traditional bare guide wire can be deployed to the location of the occlusion, e.g. as performed in a typical existing PCI procedure to treat a CTO. In step 410, catheter 100 can then be deployed over the guide wire so that distal end 102 of catheter 100 is positioned at CTO site. In such an embodiment, a lumen (e.g. lumen 130 in catheter 100) can initially be left open so that the guide wire can be used to deploy catheter 100 to the desired location. As used in typical guide wire/catheter placement, the end of the guide wire that is distal to the CTO site can be inserted into the open lumen, e.g. at distal end 102 of catheter 100. Catheter 100 can then be directed toward the CTO site until distal end 102 is positioned proximal to the location of occlusion 300.

In step 415, the guide wire can then retracted from the lumen, while the catheter 100 remains in the desired location. The desired component or components can then be inserted into the lumen that was previously used for guide wire deployment of catheter 100 in step 420 (or any open lumen, including for example vacuum aperture 160). For example, if lumen 130 were used for guide wire deployment, then imaging fiber 131 and torque coil 132 can be inserted into lumen 130. In certain embodiments, control system 200 can automatically retract the guide wire and insert the desired components.

In step 425, the user (e.g. the treating physician) can use imaging fiber 131 to visually inspect and examine occlusion 300 and the surrounding tissue. In step 430, the user can initiate cutting of material from occlusion 300 with laser fiber 141, as explained in further detail below. In step 435, catheter 100 can be advanced until it penetrates occlusion 300. After catheter 100 has penetrated occlusion 300, imaging fiber 131 (or another component) can be retracted from a lumen in step 440. This retraction can create a passageway through occlusion 300 via the open lumen from which the component was retracted. In step 445, the guide wire can be inserted into the open lumen and through the occlusion. In step 450, catheter 100 can be retracted while the guide wire remains in position extending through the occlusion. At this stage in step 455, traditional treatment techniques (e.g. expandable stents, atherectomy, etc.) can be employed using the guide wire to maintain an open passageway through the vessel that had previously been totally occluded.

Referring back now to FIG. 3, further details will be provided regarding the removal of material from occlusion 300. In this embodiment, debris material 301 that is cut from occlusion 300 can be removed from the site by a vacuum through aperture 160 (which is coupled to vacuum source 260). In particular embodiments, inert gas source 250 can direct pressurized $CO_2$ gas to the site of occlusion 300 to assist in the removal of debris material 301 that is cut from occlusion 300.

In particular embodiments, control system 200 laser 240 is pulsed through laser fiber 141 to remove material 301 from occlusion 300. In particular embodiments, each laser pulse may penetrate approximately 5 microns into occlusion 300 to "cut" material (e.g. induce a phase change in the occlusion material with electromagnetic energy) from occlusion 300, including for example calcium. In particular embodiments, laser 240 can be configured as a CLPN and CLPNT, 5-15 ns, 3 W, Cr:ZnSe/S pulsed nanosecond Mid-IR laser from IPG Photonics. In such embodiments, laser 240 can provide pulse energies up to 3 mJ, pulse duration 5-15 ns and pulse repetition rate up to 1 kHz and can be pumped by an IPG Photonics' thulium fiber laser that can provide radiation in 2.3-3.0 micron range.

In certain embodiments, control system 200 can also control the pressure from inert gas source 250 directed through lumen 150 so that the pressure is cycled on and off to correspond with operating cycles of radiation emitted from laser fiber 141 (e.g. the application of inert gas pressure is cycled to synchronize with the electromagnetic energy cycled on and off from laser fiber 141). The operating cycles of the inert gas pressure and the laser fiber are understood to be of longer duration than the pulse duration of laser 240. The pressure cycles in combination with the vacuum can therefor assist in the removal of debris material 301 from the surface of occlusion 300. In certain embodiments, the laser pulses may have a duration of 20 microseconds and a frequency of 25 Hz in certain embodiments. Pulses of gas are introduced in coordination with laser emission, and in certain embodiments, the inert gas cycling occurs at the same time as the electromagnetic energy is cycled from laser fiber 141. In particular embodiments, the inert gas cycling is timed so that it alternates with electromagnetic energy pulsing from laser fiber 141. In some embodiments, the inert gas cycling may be timed to partially overlap with application of electromagnetic energy from laser fiber 141.

Material 301 can be removed from the region via vacuum lumen 160. This approach of immediate removal of debris will avoid heating of the coronary artery by debris material 301. Heating is known to result in restenosis weeks and months after therapy and therefore minimal heat generation is desirable. Another method to minimize vessel heating is to use knowledge of the plaque or CTO composition to control the pulsed of the laser. For example, since calcium is more difficult to cut, greater laser pulse energy would be required, and would result in the greater heat generation. However, lipid and fibrous tissue would require less laser energy to cut and laser power could be reduced resulting in less energy generation based on automated plaque characterization. Knowledge of the CTO composition may be obtained from the OCT image, or by analyzing the laser ablation plume or by analyzing the debris removed with the low pressure source.

In the embodiment shown, imaging fiber 131 comprises a lens 133 at the distal end of imaging fiber 131. In particular embodiments, lens 133 may be a gradient index (GRIN) lens with an angled tip 134. In this embodiment, imaging fiber 131 can focus light 135 at a distance and also redirect light 135 at an angle to an axis 139 of fiber 131. During operation, imaging fiber 131 rotates within torque sheath 132, so that light 135 looks forward at an angle to the axis of rotation 139 and OCT imaging can be performed across the entire surface of occlusion 300. As shown in FIG. 4, imaging fiber 131 has rotated about axis 139 so that it is approximately 180 degrees from the position shown in FIG. 3. This position allows light 135 to be distributed across the lower portion of occlusion 300. Accordingly, as fiber 131 rotates during operation, the entire surface of occlusion 300 can be imaged using OCT principles.

In addition, imaging fiber 131 focuses light 135 at a distance that is greater from the distal end of the catheter than the distance laser fiber 141 focuses light 145 to remove material from occlusion 300. As shown in FIG. 3, the distance D1 from distal end 102 of catheter 100 is greater than the distance D2, where D1 represents the distance at which light 135 focused by imaging fiber 131 and D2 represents the distance at which light 145 is focused by laser fiber 141. Such a configuration focuses the OCT beam from imaging fiber 131 ahead of the light emitted from laser, so that imaging plane is ahead of the cutting plane and the wall of the blood vessel 350 is not perforated.

As shown in FIG. 3, laser fiber 141 comprises an optical element 142 that directs the energy from laser 240 toward the center of the device lumen and across the surface of occlusion 300 (e.g. by diffracting the electromagnetic energy emitted from laser fiber 141). Optical element 142 may be for example, a sapphire wedge that redirects Er:YAG laser radiation toward the center of the device lumen. In particular embodiments, the user can rotate catheter 100 via sheath 110 to orient distal end 102 radially with respect to occlusion 300. The ability to rotate catheter 100 can allow for the user to direct the electromagnetic energy from laser fiber 141 to different regions of occlusion 300. This ability may be desirable, for example, if the energy emitted from laser fiber 141 is more concentrated in areas of occlusion 300 that are proximal to laser fiber 141. In particular embodiments, optical element 142 may comprise a surface profile or phase plate 143 that reduces the emitted electromagnetic energy in the area proximal to laser fiber 141 so that the energy from laser fiber 141 is more evenly distributed across occlusion 300. Optical element 142 may also comprise an angled end 144. In particular embodiments, angled end 144 may be angled between 10 and 12 degrees (e.g. from vertical in the orientation shown in FIG. 3).

In certain embodiments, laser fiber 141 may be formed from a biocompatible material, including for example sapphire. In particular embodiments, optical element 142 may be formed from a biocompatible material. In such embodiments, laser fiber 141 may be formed from a material that may not be recognized as biocompatible, because optical element 142 (or another biocompatible plug in lumen 140) restricts material that is not biocompatible from contacting the patient tissue.

Exemplary embodiments as shown and described herein can provide significant advantages over existing techniques for addressing vascular occlusions, in particular CTOs. In addition to being small enough to allow access to areas that other devices cannot reach, the system disclosed herein includes features that can reduce procedure times. For example, exemplary embodiments provide for laser removal of CTO material over substantially all of the cross-sectional area of the occlusion in the center of the occluded vessel. In exemplary embodiments, the combination of optical element 142 at the end of laser fiber 141 and the ability to rotate catheter 100, and image with OCT fiber 131 ahead of the focus of the laser can allow a physician to direct electromagnetic energy from the laser across the surface of the central portion of the occlusion.

In addition, the delivery of a pressurized inert gas to the region via inert gas lumen 150 can assist in removal of debris material from the surface of the occlusion as it is exposed to electromagnetic energy emitted from laser fiber 141. Vacuum lumen 160 further assists in the removal of dislodged material from the occlusion, which can reduce temperature increases in the region to prevent restenosis of the vessel weeks to months later.

It is understood that while circular cross-section lumens are shown in the views of FIGS. 2 and 3, other embodiments may comprise lumens with different shape cross-sections with the goal of reducing the outer diameter of the catheter, including for example, crescent-shaped cross-sections. The use of crescent-shaped cross-section lumens could provide for greater cross-sectional areas in individual lumens, or could provide for a reduced diameter of outer sheath 110 and catheter 100. In particular embodiments, outer sheath 110 may have a diameter of approximately 1.0 mm or less, which is small enough to allow access to occlusions in restricted areas, including for example, coronary arteries.

In addition, while the embodiment described above includes insertion of the guide wire into the imaging fiber lumen, other embodiments may utilize a different lumen. For example, in certain embodiments, the guide wire may be inserted into the vacuum lumen, inert gas lumen or laser fiber lumen during use.

* * *

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 6,712,798
U.S. Pat. No. 7,004,173
U.S. Pat. No. 7,734,332
U.S. Pat. No. 8,147,414
U.S. Pat. No. 8,241,273
U.S. Pat. No. 9,125,562
U.S. Pat. No. 9,283,034
U.S. Pat. No. 9,486,143
U.S. Pat. No. 9,557,156
U.S. Pat. No. 9,572,492
U.S. Patent Publication 20100010355
U.S. Patent Publication 20100063534
U.S. Patent Publication 20110218528
U.S. Patent Publication 20140200438
U.S. Patent Publication 20140350523
U.S. Patent Publication 20150342681
U.S. Patent Publication 2017007162
PCT Patent Publication WO2017074920
"The Potential of Optical Coherence Tomography for Intravascular Imaging of Chronic Total Occlusions", Nigel R. Munce, University of Toronto Thesis, 2009.
PR Newswire "Spectranetics Initiates Research Collaboration to Combine Imaging Technology With Its Laser Devices, May 18, 2006.

The invention claimed is:

1. A method of treating a chronic total occlusion in a blood vessel, the method comprising:
    deploying a guide wire to a location of the chronic total occlusion;
    deploying a catheter over the guide wire, wherein:
        the catheter comprises a proximal end, a distal end, a plurality of lumens, and a laser fiber;
        the catheter is deployed over the guide wire via a first lumen in the plurality of lumens; and
        the distal end of the catheter is positioned at the location of the chronic total occlusion;
    retracting the guide wire from the first lumen in the catheter;
    inserting an imaging fiber into an open lumen of the catheter;
    visually inspecting the location of the chronic total occlusion via the imaging fiber ahead of a focus of the laser fiber;

cutting material from the chronic total occlusion via the laser fiber;
retracting the imaging fiber from the first lumen of the catheter;
inserting the guide wire into the first lumen of the catheter and through the chronic total occlusion;
retracting the catheter from the location of the chronic total occlusion while the guide wire remains in position extending through the chronic total occlusion; and
delivering a pressurized inert gas to the location of the chronic total occlusion, wherein:
removing material from the chronic total occlusion via the laser fiber comprises:
pulsing electromagnetic energy from the laser fiber;
delivering the pressurized inert gas to the location of the chronic total occlusion comprises pulsing the pressurized inert gas; and
using a vacuum to remove laser debris liberated by the pressurized inert gas.

2. The method of claim 1 wherein the guide wire does not enter the subintimal space of the blood vessel when the guide wire is inserted through the chronic total occlusion.

3. The method of claim 1 further comprising:
deploying an expandable stent to the location of the chronic total occlusion; and
expanding the expandable stent.

4. The method of claim 1 further comprising: deploying an atherectomy catheter to the location of the chronic total occlusion; and spinning the atherectomy catheter to further enlarge and decalcify the total occlusion.

5. The method of claim 1 wherein:
the laser fiber comprises a lens at a distal end of the laser fiber; and
wherein removing material from the chronic total occlusion via the laser fiber comprises directing electromagnetic energy through the lens and across the chronic total occlusion.

6. The method of claim 5 further comprising rotating the laser fiber to direct electromagnetic energy to different regions of the chronic total occlusion.

7. The method of claim 6 further comprising imaging via OCT light focused ahead of the laser fiber to safely direct electromagnetic energy from the laser fiber to different regions of the chronic total occlusion, but away from a wall of the blood vessel.

8. The method of claim 1 further comprising:
delivering a pressurized inert gas to the location of the chronic total occlusion.

9. The method of claim 8 wherein the pressurized inert gas comprises pressurized $CO_2$.

10. The method of claim 1 wherein pulsing electromagnetic energy from the laser fiber is synchronized with pulsing the pressurized inert gas and a vacuum.

11. The method of claim 1 wherein electromagnetic energy is pulsed from the laser fiber at a frequency of 0.1-1.0 kHZ.

12. The method of claim 1 wherein each electromagnetic energy pulse has a duration of 1-30 nanoseconds.

13. The method of claim 1 wherein each electromagnetic energy pulse has a duration of 2-20 nanoseconds.

14. The method of claim 1 wherein each electromagnetic energy pulse has a duration of 5-15 nanoseconds.

15. The method of claim 1 wherein the laser fiber emits electromagnetic energy in a range of wavelengths from 1.0-5.0 microns.

16. The method of claim 1 wherein the laser fiber emits electromagnetic energy in a range of wavelengths from 1.5-4.0 microns.

17. The method of claim 1 wherein the laser fiber emits electromagnetic energy in a range of wavelengths from 2.3-3.0 microns.

18. The method of claim 1 wherein the laser fiber emits electromagnetic energy with a pulse repetition rate of 25 Hz-1 kHz.

19. The method of claim 1 wherein the laser fiber emits electromagnetic energy with a pulse duration of 20 µs to 1 ms.

20. The method of claim 1 wherein the laser fiber emits electromagnetic energy with a wavelength of 2.94 µm.

21. The method of claim 1 wherein the laser fiber emits electromagnetic energy with a pulse energy of 1 mJ to 100 mJ.

22. The method of claim 1 wherein the laser fiber emits electromagnetic energy with a pulse energy of approximately 5 mJ.

23. The method of claim 1 wherein the laser fiber emits electromagnetic energy with an average power of 1-10 W.

\* \* \* \* \*